(12) United States Patent
Gray

(10) Patent No.: US 6,537,518 B1
(45) Date of Patent: Mar. 25, 2003

(54) PARTICULATE MATERIAL

(75) Inventor: Bruce Nathaniel Gray, Claremont (AU)

(73) Assignee: Sirtex Medical Limited, Western Australia (AU)

( * ) Notice: Subject to any disclaimer, the term of this patent is extended or adjusted under 35 U.S.C. 154(b) by 92 days.

(21) Appl. No.: 09/639,566

(22) Filed: Aug. 16, 2000

Related U.S. Application Data

(63) Continuation-in-part of application No. 09/178,259, filed on Oct. 23, 1998, now Pat. No. 6,258,338, which is a continuation of application No. 08/676,381, filed on Sep. 23, 1996, now Pat. No. 5,885,547.

(30) Foreign Application Priority Data

Jan. 21, 1994 (AU) .............................................. 54724/94

(51) Int. Cl.$^7$ ........................ A61K 51/00; A61M 36/14
(52) U.S. Cl. ...................... 424/1.29; 424/1.11; 424/9.1; 424/1.37; 424/1.33; 424/1.65
(58) Field of Search ................................ 424/1.11, 1.29, 424/1.33, 1.37, 1.65, 9.1, 9.32, 9.321, 9.323, 9.36, 9.4, 9.42, 9.5, 9.51, 9.52, 400, 450, 455, 458; 128/662.02, 660.01, 653.1; 501/1, 11, 134, 152, 153

(56) References Cited

U.S. PATENT DOCUMENTS

| | | | |
|---|---|---|---|
| 3,365,315 A | 1/1968 | Beck et al. | |
| 4,039,480 A | 8/1977 | Watson et al. | |
| 4,290,847 A | 9/1981 | Johnson et al. | |
| 4,303,433 A | 12/1981 | Torobin | |
| 4,340,642 A | 7/1982 | Netting et al. | |
| 4,349,456 A | 9/1982 | Sownan | |
| 4,411,847 A | 10/1983 | Netting et al. | |
| 4,547,468 A | 10/1985 | Jones et al. | |
| 4,772,511 A | 9/1988 | Wood et al. | |
| 4,789,501 A | 12/1988 | Day et al. | |
| 4,874,726 A | 10/1989 | Kleeb et al. | |
| 4,889,707 A | 12/1989 | Day et al. | |
| 5,011,677 A | 4/1991 | Day et al. | |
| 5,011,797 A | 4/1991 | Day et al. | |
| 5,039,326 A | 8/1991 | Day et al. | |
| 5,302,369 A | 4/1994 | Day et al. | |
| 5,885,547 A | 3/1999 | Gray et al. | |
| 6,258,338 B1 * | 7/2001 | Gray | 424/1.29 |

FOREIGN PATENT DOCUMENTS

| | | |
|---|---|---|
| EP | 0182131 | 5/1986 |
| EP | 0369638 | 5/1990 |
| GB | 2073589 | 10/1981 |
| WO | WO 8602093 | 4/1986 |
| WO | WO 9314788 | 8/1993 |

* cited by examiner

*Primary Examiner*—Dameron L. Jones
(74) *Attorney, Agent, or Firm*—Baker Botts L.L.P.

(57) ABSTRACT

A particulate material comprises hollow or cup-shaped ceramic microspheres having a diameter in the range of from 5 to 200 microns, the microspheres being formed from a base material comprising greater than 70% by weight of yttria or another yttrium-containing compound together with one or more compounds selected from the group consisting of alumina or another aluminium-containing compound, zirconia or another zirconium-containing compound, and silica or another silicon-containing compound.

The particulate material may comprise a beta-radiation emitting radionuclide ytrrium-90, and be used in selective internal radiation therapy (SIRT) of various forms of cancer and tumors.

25 Claims, No Drawings

PARTICULATE MATERIAL

This is a continuation-in-part of application Ser. No. 09/178,259 filed Oct. 23, 1998, now U.S. Pat. No. 6,258,338 which is a continuation of application Ser. No. 08/676,381 filed Sep. 23, 1996 now U.S. Pat. No. 5,885,547.

FIELD OF THE INVENTION

This invention relates to a particulate material which comprises small hollow or cup-shaped ceramic particles (hereinafter referred to as "microspheres"), to a process for the production thereof, and to methods for the use of this particulate material.

In one particular aspect, this invention relates to hollow or cup-shaped ceramic microspheres which consist of or comprise a radioactive material, and to the use of these radioactive microspheres in the treatment of cancer in humans and other mammals. In this aspect, the radioactive microspheres are designed to be administered into the arterial blood supply of the organ to be treated, whereby they become entrapped in the small blood vessels of the target organ and irradiate it. An alternate form of administration is to inject the radioactive microspheres directly into the tumour to be treated.

The particulate material of the present invention therefore has utility in the treatment of various forms of cancer and tumours, but particularly in the treatment of primary and secondary cancer of the liver and the brain. It is, however, to be understood that this invention is not limited to microspheres of radioactive material, and extends to microspheres of other ceramic materials which are suitable for use in the process described herein.

BACKGROUND OF THE INVENTION

Many previous attempts have been made to locally administer radioactive materials to patients with cancer as a form of therapy. In some of these, the radioactive materials have been incorporated into small particles, seeds, wires and similar related configurations that can be directly implanted into the cancer. In other approaches, the radioactive materials have been formulated into microspheres of regular size for injection into the arterial blood supply of the target organ. When radioactive particles or microspheres are administered into the blood supply of the target organ, the technique has become known as Selective Internal Radiation Therapy (SIRT). Generally, the main form of application of SIRT has been its use to treat cancers in the liver.

There are many potential advantages of SIRT over conventional, external beam radiotherapy. Firstly, the radiation is delivered preferentially to the cancer within the target organ. Secondly, the radiation is slowly and continually delivered as the radionuclide decays. Thirdly, by manipulating the arterial blood supply with vasoactive substances (such as Angiotensin-2), it is possible to enhance the percentage of radioactive microspheres that go to the cancerous part of the organ, as opposed to the healthy normal tissues. This has the effect of preferentially increasing the radiation dose to the cancer while maintaining the radiation dose to the normal tissues at a lower level (Burton, M. A. et al.; Effect of Angiotensin-2 on blood flow in the transplanted sheep squamous cell carcinoma. *Europ. J. Cancer Clin. Oncol.* 1988, 24(8):1373–1376).

When microspheres or other small particles are administered into the arterial blood supply of a target organ, it is desirable to have them of a size, shape and density that results in the optimal homogeneous distribution within the target organ. If the microspheres or small particles do not distribute evenly, and as a function of the absolute arterial blood flow, then they may accumulate in excessive numbers in some areas and cause focal areas of excessive radiation. It has been shown that microspheres of approximately 25–50 micron in diameter have the best distribution characteristics when administered into the arterial circulation of the liver (Meade, V. et al; Distribution of different sized microspheres in experimental hepatic tumours. *Europ. J. Cancer & Clin. Oncol.* 1987, 23:23–41).

If the microspheres or small particles do not contain sufficient ionising radiation, then an excessive number will be required to deliver the required radiation dose to the target organ. It has been shown that if large numbers of microspheres are administered into the arterial supply of the liver, then they accumulate in and block the small arteries leading to the tumour, rather than distribute evenly in the capillaries and precapillary arterioles of the tumour. Therefore, it is desirable to use the minimum number of microspheres that will provide an even distribution in the vascular network of the tumour circulation.

Similarly if the microspheres or small particles are too dense or heavy, then they will not distribute evenly in the target organ and will accumulate in excessive concentrations in parts of the liver that do not contain the cancer. It has been shown that solid heavy microspheres distribute poorly within the parenchyma of the liver when injected into the arterial supply of the liver. This, in turn, decreases the effective radiation reaching the cancer in the target organ, which decreases the ability of the radioactive microspheres to kill the tumour cells. In contrast, microspheres distribute well within the liver (Burton, M. A. et al.; Selective International Radiation Therapy; Distribution of radiation in the liver. *Europ. J. Cancer Clin. Oncol.* 1989, 25:1487–1491).

For radioactive microspheres to be used successfully for the treatment of cancer, the radiation emitted from the microspheres should be of high energy and short range. This ensures that the energy emitted from the microspheres will be deposited into the tissues immediately around the microspheres and not into tissues which are not the target of the radiation treatment. There are many radionuclides that can be incorporated into microspheres that can be used for SIRT. Of particular suitability for use in this form of treatment are the unstable isotopes of yttrium (Y-90) and phosphorous (P-32), although other isotopes such as iodine can also be used. Yttrium-90 is the unstable isotope of yttrium-89 which can be manufactured by placing the stable yttrium-89 in a neutron beam. The yttrium-90 that is generated decays with a half life of 64 hours, while emitting a high energy pure beta radiation.

If the microspheres contain other radioactive substances that are not required for the radiation treatment of the target tissue, then unwanted and deleterious radiation effects may occur. It is therefore desirable to have microspheres of such a composition that they only contain the single desired radionuclide. In this treatment mode, it is desirable to have microspheres that emit high energy but short penetration beta-radiation which will confine the radiation effects to the immediate vicinity of the microspheres. For this purpose, yttrium-90 is the preferred radionuclide.

Therefore, the ideal microspheres for use in this treatment mode will have a low density relative to pure yttria, be in the size range of from 20–80 micron, and be stable so that no material leaches from the microspheres when administered into the body of a human or other mammalian patient.

In the earliest clinical use of yttrium-90-containing microspheres, the yttrium was incorporated into a polymeric matrix that was formulated into microspheres. While these microspheres were of an appropriate density to ensure good distribution characteristics in the liver, there were several instances in which the yttrium-90 leached from the microspheres and caused inappropriate radiation of other tissues.

In one attempt to overcome the problem of leaching, a radioactive microsphere comprising a biologically compatible glass material containing a beta- or gamma-radiation emitting radioisotope such as yttrium-90 distributed throughout the glass, has been developed (International Patent Publication No. WO 86/03124).

There have been several reports of clinical studies on the use of solid glass radioactive microspheres. In one report, ten patients with primary hepatocellular carcinoma were treated, however no patient had a complete or partial response (Shepherd, F. et al., Cancer, Nov. 1, 1992, Vol.70, No.9, pp 2250–2254).

A further development in order to overcome the problem of leaching, was the production of light polymeric ion-exchange microspheres that did not leach their yttrium content when injected into the body. Using these microspheres, a high objective response rate for patients with secondary cancer in the liver was obtained when the microspheres were injected into the hepatic artery (Gray, B. N. et al. Regression of liver metastases following treatment with Yttrium-90 microspheres. *Aust. N.Z. J. Surg.* 1992, 62:105–110). One disadvantage of such polymeric ion exchange microspheres is that the yttrium-90 radionuclide must be added to the microsphere after neutron activation of the stable isotope of yttrium-89. This requires the use of specialised facilities and potentially is hazardous to the manufacturing personnel. Furthermore, the polymeric microspheres contain only a low percentage of yttrium.

Using the technique described by Gray et al., other clinical studies in patients with secondary liver cancer have demonstrated a very high response rate using yttrium-90 containing microspheres. In one study in patients with metastatic liver cancer, the majority of patients benefited from treatment with radioactive microspheres with appropriate physical characteristics, especially when combined with perfusion of cytotoxic drugs into the arterial circulation of the liver (Gray, B. N. et al., supra).

SUMMARY OF THE INVENTION

In one aspect, the present invention provides a particulate material comprising hollow or cup-shaped ceramic microspheres having a diameter in the range of from 5 to 200 microns, said microspheres being formed from a base material comprising greater than 70% by weight of yttria or another yttrium-containing compound together with one or more compounds selected from the group consisting of alumina or another aluminium-containing compound, zirconia or another zirconium-containing compound, and silica or another silicon-containing compound.

Preferably, the base material comprises at least 75% by weight, more preferably at least 80% by weight, and even more preferably at least 85% by weight, of yttria or another yttrium-containing compound.

Preferably also, the microspheres have a diameter in the range of from 20 to 80 microns.

A further preferred feature of the particulate material of the present invention is that the microspheres have a density in the range of from 1 to 4 gm/cm$^3$, more preferably in the range of from 1 to 3 gm/cm$^3$.

The microspheres may comprise yttria together with alumina, zirconia or silica, or combinations thereof, as ceramic base material. In addition to the oxides mentioned above, other compounds, including salts, containing yttrium, aluminium, zirconium or silicon which are suitable for forming the particulate material of this invention may also be used as the base material.

In a particularly preferred embodiment of this invention, the microspheres comprising yttria or another yttrium-containing compound or salt of yttrium as a base material component thereof may be rendered radioactive by exposure to a neutron beam that activates the yttria or yttrium-containing base to the material radionuclide yttrium-90. These preferred microspheres do not leach the base material of which they are composed, and are biologically compatible.

The present invention further extends to a radioactive particulate material comprising hollow or cup-shaped ceramic microspheres having a diameter within the range of from 5 to 200 microns and comprising a beta or gamma-radiation emitting radionuclide, said microspheres being formed from a base material comprising greater than 70% by weight of yttria or another yttrium-containing compound together with one or more compounds selected from the groups consisting of alumina or another aluminium-containing compound, zirconia or another zirconium-containing compound, and silica or another silicon-containing compound.

Preferably, the beta-radiation emitting radionuclide is yttrium-90.

The present invention also provides a method of radiation therapy of a human or other mammalian patient, which comprises administration to the patient of a radioactive particulate material as described above.

Preferably, the therapy comprises treatment of cancer or tumours, particularly primary or secondary cancer of the liver, in the patient.

DETAILED DESCRIPTION OF THE INVENTION

In order to overcome the problem of leaching of radionuclide from ceramic microspheres, while at the same time maintaining the microspheres with a low density, the present invention provides microspheres with improved characteristics arising from the fact that the microspheres are either hollow or cup-shaped. These microspheres can be formulated to be of such a size, shape and density that they have improved distribution characteristics when administered into the arterial supply of target organs to be treated. In addition, as they comprise greater than 70% by weight yttria, each microsphere can deliver a higher amount of ionising radiation than prior art microspheres. This, in turn, means that a lesser number can be administered to the target organ in order to deliver the same radiation dose. In another improvement, the microspheres can be neutron activated after manufacture, thereby improving the manufacture process.

The inclusion of aluminosilicate or other glass with yttria in the microspheres of the present invention facilitates the formation of voids within the hollow or cup-shaped microspheres. This may be due to the fact that aluminosilicate glasses melt at a lower temperature than yttria and have greater plastic qualities at moderately high temperatures. This would allow early melting of the particulate glass base material which is an intrinsic step in the formation of the void. Thus, as the outer regions of the yttria/glass aggregates melt and become plastic, they would rapidly fuse into a shell which would then be blown up more easily than if the aggregate was made of pure yttria.

In one aspect of the invention, the microspheres may be produced by a process which involves the grinding of yttria and glass particles to a powder, the aggregation of the powder into small aggregates held together by a binder, and then the passage of the aggregate through a flame that is hot enough to rapidly melt the glass-yttria aggregate. This will also cause the microparticle to blow up into a hollow bubble containing a void in the centre.

In an alternative process, described in detail below, the plasma spraying technique is used for forming hollow microspheres. Yet other processes replace the plasma spraying with other methods of heating, such as heating in a rotary kiln or the passage of the aggregate through a hot flame that is hot enough to melt the glass component of the aggregate.

In the following detailed description, reference is made in particular to the production and use of hollow or cup-shaped yttria/aluminosilicate glass microspheres in accordance with this invention. It is to be understood, however, that this description is equally applicable to the production of similar microspheres using other suitable ceramic base materials as described above.

In the production of hollow or cup-shaped ceramic microspheres in accordance with this invention, aggregates or agglomerates of powdered ceramic base material with a suitable binder material are formed. The purpose of the binder is to provide enough adhesive quality and strength to stabilise the aggregates, preferably in substantially spherical form. The maximum particle size of the aggregates is generally approximately 75 microns, and typically is in the range of 5 to 50 microns. The particulate size should be as uniform as possible to achieve best results in subsequent processing. Preferably, the aggregates are formed by agglomeration of fine powdered ceramic base material (for example, powder of approximately 0.1 up to several microns) using the spray drying technique in which the fine powder is mixed with a suitable binder and liquid to form a slurry. The slurry is then pumped to an atomiser where it is broken up into a large number of small droplets and dried using hot air to produce the resultant aggregates, generally in substantially spherical form.

The aggregates are then heated to melt the base material, preferably using the process of thermal or plasma spraying (for example, using a D.C. plasma jet) in which very high temperatures of approximately 17000° C. may be attained to ensure complete melting of the ceramic base material and vaporisation or volatilisation of the binder material. In plasma spraying the aggregates are introduced using a carrier gas such as argon into the plasma torch which uses a high temperature plasma such as argon, helium, hydrogen, or nitrogen, or mixtures thereof in the form of a plasma. The ceramic base material becomes molten and is then accelerated to a high velocity to be subsequently rapidly solidified, for example by collection in a body of water. During the plasma spraying, hollow or cup-shaped particles are formed due to the presence of large gas bubbles trapped within the molten material.

After solidification, yttria/aluminosilicate glass microspheres can then be irradiated in a neutron beam to result in the formation of the radioactive isotope yttrium-90 which is suitable for administration to patients.

During the production process, some microspheres do not form hollow spheres but take on a cup-shaped configuration. The cup-shaped particles are of similar size to the hollow microspheres. The presence of these cup-shaped particles does not significantly alter the characteristics of the batch of microspheres that are produced, and mixtures of both hollow and cup-shaped microspheres can be used for administration to patients. The invention therefore also includes the production of cup-shaped microspheres of a size distribution similar to that of hollow microspheres. In addition, whilst some microspheres may contain only one hollow pore or void, others may contain more than one such hollow pore or void. Once again, the presence of more than one pore in these hollow microspheres does not significantly alter the characteristics of the microspheres and accordingly the term "hollow microsphere" as used herein is to be understood as encompassing both microspheres with a single hollow pore or void, and microspheres with more than one hollow pore or void.

The thermal spraying technique results in microspheres with a variable size range. Microspheres of the desired size of from 5 to 200 micron can be sorted by a process of sieving, or using other well described techniques for sorting of small particles based on size. Similarly, the microspheres can be sorted into batches of similar density using conventional techniques for separating particles on the basis of density.

One example of a suitable binding material which may be used to bind the powdered base material during the spray drying process is polyvinyl alcohol. It will be appreciated that other binding materials can also be used to bind the base material for spray drying. The amount of binder material which is used may be varied as desired. Typically, however amounts of binder material of between 0.5 and 8 wt %, based on the dry weight of the powdered ceramic base material, may be used.

Preferably, yttria/aluminosilicate glass microspheres are produced by first grinding the base material to a fine powder, for example up to several microns in diameter, and then spray drying the powder in the form of a slurry to form aggregates of the base material. The slurry contains a binding material, such as PVA, which allows the formation of aggregates when fed through a spray drying apparatus. The spray dried aggregates can then be fed into a thermal jet (e.g. D.C. plasma jet) which results in the melting of the spray dried particles. The binding material used in the slurry during the spray drying process vaporises in the thermal jet during the process of melting and distends the microspheres into the form of hollow or cup-shaped particles. The particles are then solidified, preferably by collection in a cold medium such as water.

In one embodiment of this invention, there are provided hollow or cup-shaped microspheres with the desired shape and density for use in the treatment of various forms of cancer and tumours, particularly in the liver and brain. The preferred microspheres are composed of yttria/aluminosilicate glass, with a preferred size range of from 20 to 80 micron in diameter. The hollow or cup-shaped microspheres are placed in a neutron beam to activate the yttria to the unstable isotope yttrium-90, and the radioactive microspheres can then be used in the treatment of cancers and/or tumours as described above.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Further features of the present invention are more fully described in the following Examples. It is to be understood, however, that this detailed description is included solely for the purposes of exemplifying the present invention, and should not be understood in any way as a restriction on the broad description of the invention as set out above.

EXAMPLE 1

150 g of yttria is mixed with 50 g of K1 glass microspheres by placing the powders in a 2 L sealed plastic container with ten stainless steel balls (12 mm diameter) and shaking the container vigorously for two minutes. The mixed yttria-glass powder is then heat treated at 1200° C. for 1 hour to melt the glass, then the resulting melt ground to a powder and sized using 125 m and 32 m sieves. A 40 g sample from this size fraction is flame-sprayed by passing the powder through a neutral oxygen/acetylene flame under gravity feed into a stainless steel collection bucket containing water. The flame-sprayed product is wet-sieved through 125 m and 32 m sieves, and the 32–125 m fraction retained for microscopy.

In a further experiment, the mixed yttria-glass powder produced as described above, is fed into a DC plasma torch. A Plasmadyne SG-100 torch may be used with an arc gas of argon/helium gas flow using argon as the carrier gas, under the following conditions:

| Arc Gas Flow Rate: | |
|---|---|
| Argon (L/min) | 40 |
| Helium | 4 |
| Current (Amps) | 900 |
| Voltage (Volts) | 44.4 |
| Carrier Gas | Argon |

The above conditions have been determined to be the optimal torch conditions and powder conditions to produce hollow microspheres with a size range from 20 to 80 micron. Various other plasma torch conditions can be used with different current and voltage rates.

A range of hollow spherical particles that contain the combination of aluminosilicate glass and yttria may be formed, and these particles will be suitable for activation in a neutron beam which will cause activation of the yttrium to yttrium-90. The size and density of the resulting yttria/aluminosilicate glass microspheres can be varied to meet any required specification from 5 to 200 micron (more particularly 20 to 80 micron) in size, and a density of from 1 to 3 gm/cm$^3$.

The mixing of an aluminosilicate or other glass with the yttria prior to forming the hollow spherical particles improves the yield from the plasma/flame spraying, and facilitates the formation of particles containing a void within the microsphere.

Optical microscopy may be used to confirm that the yttria/aluminosilicate glass particles formed are spherical and contain substantial voids. Under transmitted light, the presence of voids within the spheres is indicated by a bright central area in the particle when the focal plane is adjusted to the middle of the sphere.

EXAMPLE 2

The yttria/aluminosilicate glass microspheres (produced in accordance with Example 1) are placed in a neutron beam to produce the beta-radiation emitting radionuclide yttrium-90.

EXAMPLE 3

The technique of Selective Internal Radiation Therapy (SIRT) has been described above. It involves either a laparotomy to expose the hepatic arterial circulation or the insertion of a catheter into the hepatic artery via the femoral, brachial or other suitable artery. This may be followed by the infusion of Angiotensin-2 into the hepatic artery to redirect arterial blood to flow into the metastatic tumour component of the liver and away from the normal parenchyma. This is followed by embolisation of yttrium-90 containing yttria/aluminosilicate glass microspheres (produced in accordance with Example 2) into the arterial circulation so that they become lodged in the microcirculation of the tumour. Repeated injections of microspheres are made until the desired radiation level in the normal liver parenchyma is reached. By way of example, an amount of yttrium-90 activity that will result in an inferred radiation dose to the normal liver of approximately 80 Gy may be delivered. Because the radiation from SIRT is delivered as a series of discrete point sources, the dose of 80 Gy is an average dose with many normal liver parenchymal cells receiving much less than that dose.

The measurement of tumour response by objective parameters including reduction in tumour volume and serial estimations of serum carcino-embryonic antigen (CEA) levels, is an acceptable index of the ability of the treatment to alter the biological behaviour of the tumour.

What is claimed is:

1. A particulate material comprising hollow or cup-shaped ceramic microspheres having a diameter in the range of from 5 to 200 microns, said microspheres being formed from a base material comprising greater than 70% by weight of yttria or another yttrium-containing compound together with one or more compounds selected from the group consisting of alumina or another aluminium-containing compound, zirconia or another zirconium-containing compound, and silica or another silicon-containing compound.

2. A particulate material according to claim 1 wherein said base material comprises at least 75% by weight of yttria or another yttrium-containing compound.

3. A particulate material according to claim 2, wherein said base material comprises at least 80% by weight of yttria or another yttrium-containing compound.

4. A particulate material according to claim 3, wherein said base material comprises at least 85% by weight of yttria or another yttrium-containing compound.

5. A particulate material according to claim 1, wherein the microspheres have a diameter in the range of from 20 to 80 microns.

6. A particulate material according to claim 1, wherein the microspheres have a density in the range of from 1 to 4 gm/cm$^3$.

7. A particulate material according to claim 6, wherein the microspheres have a density in the range of from 1 to 3 gm/cm$^3$.

8. A radioactive particulate material comprising hollow or cup-shaped ceramic microspheres having a diameter with a range of from 5 to 200 microns and comprising a beta or gamma-radiation emitting radionuclide, said microspheres being formed from a base material comprising greater than 70% by weight of yttria or another yttrium-containing compound together with one or more compounds selected from the group consisting of alumina or another aluminium-containing compound, zirconia or another zirconium-containing compound, and silica or another silicon-containing compound.

9. A radioactive particulate material according to claim 8, wherein said beta-radiation emitting radionuclide is yttrium-90.

10. A radioactive particulate material according to claim 8, wherein said base material comprises at least 75% by weight of yttria or another yttrium-containing compound.

11. A radioactive particulate material according to claim 10, wherein said base material comprises at least 80% by weight of yttria or another yttrium-containing compound.

12. A radioactive particulate material according to claim 11, wherein said base material comprises at least 85% by weight of yttria or another yttrium-containing compound.

13. A radioactive particulate material according to claim 8, wherein the microspheres have a diameter in the range of from 20 to 80 microns.

14. A radioactive particulate material according to claim 8, wherein the microspheres have a density in the range of from 1 to 4 gm/cm$^3$.

15. A radioactive particulate material according to claim 14, wherein the microspheres have a density in the range of from 1 to 3 gm/cm$^3$.

16. A method of radiation therapy of a human or other mammalian patient, which comprises administration to the patient of a radioactive particulate material comprising hollow or cup-shaped ceramic microspheres having a diameter in the range of from 5 to 200 microns and comprising a beta or gamma-radiation emitting radionuclide, said microspheres being formed from a base material comprising greater than 70% by weight of yttria or another yttrium-containing compound together with one or more compounds selected from the group consisting of alumina or another aluminium-containing compound, zirconia or another zirconium-containing compound, and silica or another silicon-containing compound.

17. A method according to claim 16, wherein said beta-radiation emitting radionuclide is yttrium-90.

18. A method according to claim 16, wherein the microspheres have a diameter in the range of from 20 to 80 microns.

19. A method according to claim 16, wherein the radiation therapy comprises treatment of cancer or tumours in the patient.

20. A method according to claim 19, wherein the radiation therapy comprises treatment of primary or secondary cancer of the liver of the patient.

21. A method according to claim 16, wherein the base material of said microspheres comprises at least 75% by weight of yttria or another yttrium-containing compound.

22. A method according to claim 21, wherein the base material of said microspheres comprises at least 80% by weight of yttria or another yttrium-containing compound.

23. A method according to claim 22, wherein the base material of said microspheres comprises at least 85% by weight of yttria or another yttrium-containing compound.

24. A method according to claim 16, wherein the microspheres have a density in the range of 1 to 4 gm/cm$^3$.

25. A method according to claim 24, wherein the microspheres have a density in the range of 1 to 3 gm/cm$^3$.

* * * * *

UNITED STATES PATENT AND TRADEMARK OFFICE
CERTIFICATE OF CORRECTION

PATENT NO. : 6,537,518 B1
DATED : March 25, 2003
INVENTOR(S) : Gray, Bruce Nathaniel It is certified that error appears in the above-identified patent and that said Letters Patent is hereby corrected as shown below:

<u>Title page,</u>
Item [57], ABSTRACT,
Line 11, "ytrrium-90" should read -- yttrium-90 --

<u>Column 7,</u>
Line 10, "125 m" should read -- 125 µm --; and "32 m" should read -- 32 µm --
Line 15, "125 m" should read -- 125 µm --; "32 m" should read -- 32 µm --; and 32-125 m" should read -- 32-125 µm --

Signed and Sealed this

Second Day of December, 2003

JAMES E. ROGAN
*Director of the United States Patent and Trademark Office*